United States Patent [19]

Fischell

[11] Patent Number: 4,594,058
[45] Date of Patent: Jun. 10, 1986

[54] SINGLE VALVE DIAPHRAGM PUMP WITH DECREASED SENSITIVITY TO AMBIENT CONDITIONS

[75] Inventor: Robert E. Fischell, Silver Spring, Md.

[73] Assignee: The Johns Hopkins University, Baltimore, Md.

[21] Appl. No.: 801,513

[22] Filed: Nov. 26, 1985

Related U.S. Application Data

[63] Continuation of Ser. No. 616,256, Jun. 1, 1984, abandoned.

[51] Int. Cl.$^4$ ............................................. F04B 43/00
[52] U.S. Cl. .................................... 417/413; 417/417; 417/557; 417/559; 128/DIG. 12; 604/123; 604/153; 92/99
[58] Field of Search ............... 417/413, 417, 557, 559, 417/395; 128/DIG. 12, DIG. 13; 604/123, 126, 153; 92/60, 99, 104

[56] References Cited

U.S. PATENT DOCUMENTS

| | | | |
|---|---|---|---|
| 2,474,349 | 6/1949 | Dickey et al. | 417/417 |
| 2,819,678 | 1/1958 | Nordell et al. | 417/570 |
| 2,854,992 | 10/1958 | Hewitt | 604/126 |
| 2,856,148 | 10/1958 | Heathcote et al. | 251/127 |
| 3,039,399 | 6/1962 | Everett | 92/99 |
| 3,168,111 | 2/1965 | Strauss | 137/625.3 |
| 3,200,757 | 8/1965 | Steffes | 92/99 |
| 3,411,704 | 11/1968 | Hilgert et al. | 417/413 |
| 3,868,973 | 3/1975 | Bierman et al. | 138/43 |
| 4,021,152 | 5/1977 | Toyoda | 417/417 |
| 4,047,852 | 9/1977 | O'Connor et al. | 417/417 |
| 4,152,098 | 5/1979 | Moody et al. | 417/417 |

FOREIGN PATENT DOCUMENTS

| | | | |
|---|---|---|---|
| 1015783 | 10/1952 | France | 92/99 |
| 1149743 | 12/1957 | France | 92/99 |
| 871344 | 6/1961 | United Kingdom | 417/395 |
| 1256070 | 12/1971 | United Kingdom | 417/395 |

Primary Examiner—Carlton R. Croyle
Assistant Examiner—Donald E. Stout
Attorney, Agent, or Firm—Robert E. Archibald; Howard W. Califano

[57] ABSTRACT

A single valve diaphragm pump is disclosed which generally includes: a pump housing, a flexible diaphragm reciprocally movable in the pump housing; an inlet filter means; and, an outlet valve. The flexible diaphragm conforms in shape to a portion of the pump housing when the diaphragm is in its actuation or rest position. The pump eliminates an inlet check valve and replaces it with an inlet filter means. The invented pump has a stroke volume which is extremely constant even though ambient pressure and reservoir pressure may vary over a considerable range. Furthermore, the invented pump provides a practical means for preventing gas bubbles from entering into the pump chamber. The invented pump can have application as a medication pump for use external to or implanted within a living body.

11 Claims, 5 Drawing Figures

PRIOR ART PUMP

PRIOR ART PUMP

PRIOR ART PUMP

SINGLE VALVE DIAPHRAGM PUMP WITH DECREASED SENSITIVITY TO AMBIENT CONDITIONS

This is a continuation of co-pending application Ser. No. 616,256 filed on June 1, 1984, now abandoned.

BACKGROUND AND/OR ENVIRONMENT OF THE INVENTION

1. Field of the Invention

In the art of pumping liquids it is frequently desirable to provide precise flow rates. A comparatively recent application of pumps is for the controlled flow of medication into humans or animals for the treatment of a variety of physiologic dysfunctions or disease. These medication pumps are being used both externally to the living body, as well as implanted within the living body.

2. Description of the Contemporary and/or Prior Art

With the acceptance of both external and implantable infusion devices, researchers have been attempting to develop a pump which satisfies the strict performance requirements imposed on these devices. It can be seen from an article written by W. J. Spencer entitled "A Review of Programmed Infusion Delivery Systems" (IEEE Transactions on Biomedical Engineering, Vol. BME-28, No. 3, March 1981) that the ideal pump would provide uniform delivery of medication in a reliable and reproducible manner with a minimum of power, weight, and volume. In an effort to meet these requirements the above-referenced article points out that current researchers are experimenting with syringe, peristaltic, piezoelectric and bellows type pumps.

The bellows or positive displacement pump appears to be an attractive type of pump for infusion devices. A patent issued to Peer M. Portner et al (U.S. Pat. No. 4,265,241, issued May 5, 1981) discloses a bellows pump consisting of a piston bellows which is actuated by a solenoid controlled armature. Movement of the piston bellows tends to increase or decrease the volume of the pumping chamber. When the volume of the pump chamber is a maximum, medication is forced from a reservoir, which is maintained at positive pressure, through an input check valve into the pump chamber. When the bellows piston is actuated, the pump chamber is at a minimum volume and fluid is forced out of the chamber through an output check valve. A patent issued to R. E. Fishell (U.S. Pat. No. , 4,373,527, issued Feb. 15, 1983) describes a bellows pump which uses the pumping action of the bellows to draw medication from a reservoir through an input check valve and into the pump chamber. When the bellows is extended by a solenoid, medication in the pumping chamber is forced from the pumping chamber via an output check valve. Similarly, U.S. Pat. No. 4,360,019, issued on Nov. 23, 1981 to Portner et al, describes a positive displacement pump which uses an elastometric diaphragm which is driven by a solenoid via a plunger. Movement of a diaphragm varies the volume in the pump chamber which causes fluid to flow into the chamber via a spring loaded input valve or to flow from the chamber via a spring loaded output valve. U.S. Pat. No. 4,152,098, issued to Norman F. Moody et al, on May 1, 1979, discloses a pump having a diaphragm which forms the inlet valve, outlet valve, and is the moveable member which varies the volume in the pumping chamber. A solenoid actuated ball is driven in contact with the diaphragm to vary the volume in the pumping chamber. Although the diaphragm remains in conformity with the ball, differential pressure across the input valve will cause the stroke volume of this prior art pump to vary.

Several of the above-cited references teach the use of a compliant diaphragm or bellows which result in variations in pump stroke volume with changes in the reservoir pressure or in ambient pressure conditions. Variations in reservoir or ambient pressure conditions will cause the diaphragm or the bellows to be deformed such that variations between the actuation and rest volumes of the pump chamber can vary considerably. Similarly, all of the above-cited references teach the use of input and output valves. Since the flow rate through the valve depends upon differential pressure across the valve, the flow rate through the input valve and therefore the stroke volume is dependent upon ambient pressure and reservoir pressure. Therefore, the prior art research and experimentation with various types of pumps has not provided a positive displacement pump which has a constant stroke volume and which is independent of ambient and reservoir pressures.

Prior research also indicates that bellows, or positive displacement pumps, are inoperable if bubbles enter the pumping chamber. If a large enough bubble enters the pumping chamber it will stop the pumping of an incompressible liquid because the gas can compress fully before sufficient pressure is generated to open the inlet and/or outlet valves. Prior art references such as U.S. Pat. No. 4,191,181, issued to Manfred Franetzki et al, on Mar. 4, 1981, attempts to solve this problem by using a wicklike member composed of lightly packed glass-like fibers which have sufficient capillary forces to prevent gas from entering the fine channels. Similarly, U.S. Pat. No. 4,360,019, referenced earlier, attempts to solve this problem by using a looped tube that terminates a short distance from the side of the straight portion of the tube. This distance, is smaller than the diameter of air bubbles, thus blocking their entry into the tube. However, the difficulty with these prior art techniques is that particulates formed in the reservoir chamber can block the filter or wick after a period of operation and thereby block medication delivery.

SUMMARY OF THE INVENTION

The present inventor recognized the above-referenced difficencies in the prior art and developed a positive displacement pump which can deliver precise and constant stroke volumes. The invented pump has a stroke volume which is extremely constant even though ambient pressure and reservoir pressure may vary over a considerable range. Furthermore, the invented pump provides a practical means for preventing gas bubbles from entering into the pumping chamber.

To solve the first above-stated problem associated with the prior art, mainly the variation in stroke volume due to the deflection of the flexible diaphragm, the present invention provides a rigid housing which contours the flexible diaphragm. The invention discloses a pump housing having an upper and lower portion. The flexible diaphragm is operably attached to the housing between the upper and lower portions and is reciprocally moveable from a rest position where the pump chamber has a maximum volume to an actuation positon where the pump chamber has a minimum volume. When in a rest position the diaphragm conforms to the contour of the inner surface to the upper portion of the housing. In this rest position the pump chamber will have a constant maximum volume regardless of reservoir ambient pressure. When the diaphragm is moved into the actuation position, it conforms to the contours of the inner surface of the lower portion of the pumping housing. In this actuation position the pump chamber will have a certain minimum volume regardless of ambient or reservoir pressure. Since the minimum and maximum volumes of the pump chamber are constant, a constant volume of fluid will be pumped each time the invented pump is actuated. The patient and physician can thus be confident that a constant volume of medication will be delivered each time the invented pump is actuated.

To solve the second above-stated problem associated with the prior art pumps, mainly the variation in stroke volume caused by differential pressure across the input valve, the present invention eliminates the inlet check valve and replaces it with an inlet filter means. The inlet filter means has a high resistance to fluid flow and in the preferred embodiment is a ceramic filter. The inlet filter means eliminates the differential flow problem associated with the prior art inlet valve and thereby allows a more constant stroke volume. The inlet filter means has the additional advantage of blocking gas bubbles from entering the pumping chamber. Also, as will be explored later in the specification, back flow into the reservoir through the inlet filter means has the tendency of cleaning the filter from particulate blockage.

In operation, the diaphragm is maintained in the rest position by a spring force. Upon actuation by a solenoid, the diaphragm is rapidly moved to the actuation position where it conforms to the shape of the inner surface of the lower portion of the pump housing. Movement of the pump diaphragm to the actuation position causes the medication to be forced out of the pump chamber through the output check valve. The inlet filter means, having a very high resistance to flow, will allow a small amount of fluid to go out through the reservoir on the down stroke. When the solenoid is no longer energized, spring action causes the diaphragm to return to its rest position where it conforms to the shape of the inner wall of the upper pump housing. As the liquid is drawn from the reservoir, the diaphragm moves upward until it sits in the rest position. The resistance of the filter is sufficiently high so that the upstroke of the pump requires as long as from 0.1 second to several seconds.

A novel feature of the present invention is the use of a flexible diaphragm which conforms to the contours of the inner surface of the pump housing when the diaphragm is in its rest and actuation positions. This feature assures that the pump will deliver a constant volume of medication regardless of ambient or reservoir pressure.

A second novel feature of the invented pump is the use of an inlet filter means which eliminates stroke volume variations caused by differential pressure across an inlet check valve. This feature also assures that a constant volume of medication will be delivered with each pump actuation regardless of ambient or reservoir pressure.

A third novel feature is the use of an inlet filter means which prevents gas bubbles from entering the pumping chamber and which allows a backflow of fluid through the inlet filter means which dislodges any particulates which might otherwise clog the filter.

A fourth novel feature of the present invention is to eliminate the inlet check valve thereby reducing the cost and total height of the pump and improving the pump's reliability. This feature is extremely important for implantable pumps.

BRIEF DESCRIPTION OF THE DRAWINGS

In order that the present invention may be more fully understood, it will now be described, by way of example, with reference to the accompanying drawings in which:

FIG. 4 shows the pump in its rest position and FIG. 5 shows the pump in its actuated position.

DESCRIPTION OF THE PREFERRED EMBODIMENT

Figure 1:
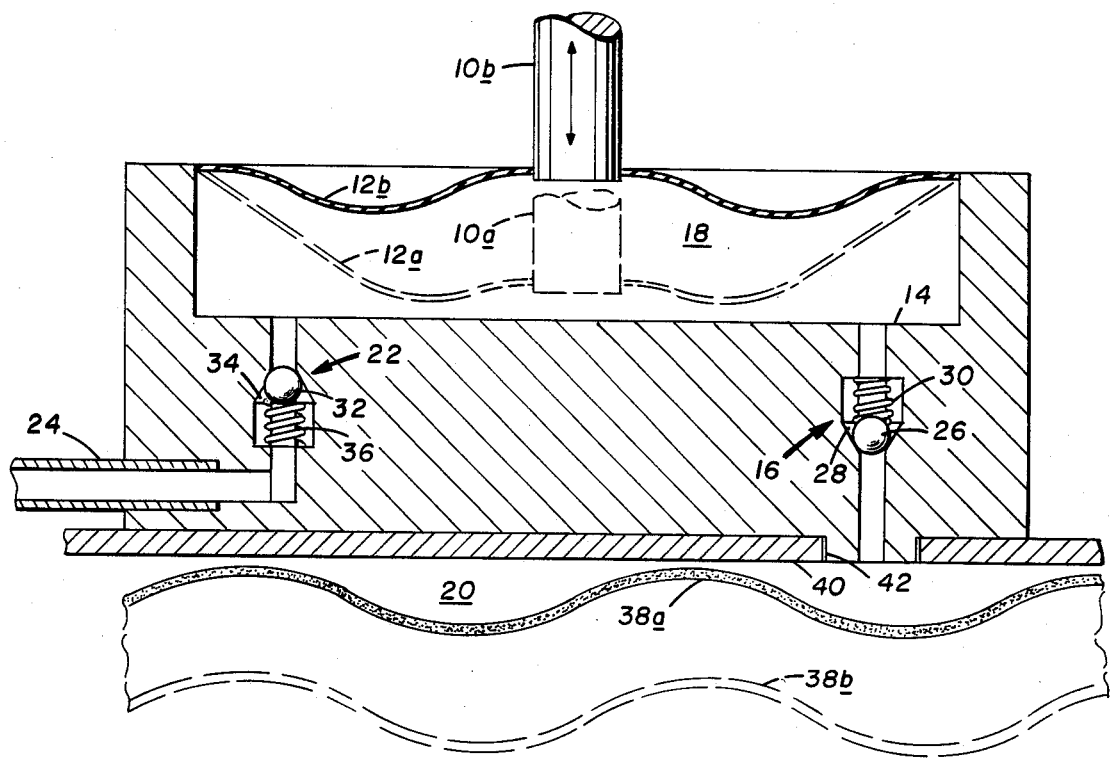
FIG. 1 illustrates a conventional prior art diaphragm pump having an inlet and an outlet valve.

The improvements of the present invention are best explained with the aid of FIG. 1 which shows a conventional prior art diaphragm pump as might be used in an implantable medication infusion system. The pump diaphragm is actuated by a solenoid (not shown) connected to a cylinder, which is shown in its normal rest (down) position at 10$a$ and in its actuated (up) position at 10$b$. The cylinder is typically actuated by a magnetic solenoid that moves the cylinder from 10$a$ to 10$b$ when actuated. The diaphragm at position 12$a$ is at its rest position and the diaphragm at 12$b$ shows its actuated position. When the diaphragm attached to the pump body 14, moves from postion 12$a$ upward, the inlet valve 16 opens and remains open until the diaphragm reaches the uppermost extent of its travel at 12$b$. In this action, the pump chamber 18 increases in volume as liquid flows from the reservoir 20 through the inlet valve 16. At the top of its stroke with the diaphragm at 12$b$, the valve 16 closes, and the spring action of the diaphragm itself (or of a separate spring that is not shown) causes the pump chamber 18 to decrease in volume thereby forcing liquid through the outlet valve 22. The diaphragm then goes to its full downward (rest) position 12$a$. Thus liquid is pumped from the reservoir 20 through the inlet valve 16, through the pump chamber 18, through the exit valve 22, and finally into the exit tube 24. It should be noted that the inlet valve 16 has a poppet 26 which closes against the valve seat 28 under the force of the valve spring 30. Likewise, the exit valve 22 has a poppet 32, a valve seat 34, and a spring 36.

Figure 2:
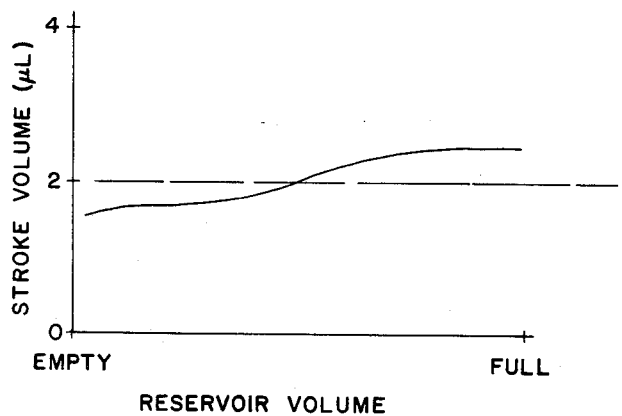
FIG. 2 is a graph showing the effect of reservoir volume on the stroke volume for prior art pulsatile pumps.

The reservoir 20 in FIG. 1 has a metallic diaphragm shown in its empty position at 38$a$ and in its full position at 38$b$. The reservoir has an upper plate 40 and has a weld 42 to attach the upper plate 40 of the reservoir 20 to the pump body 14. If the metallic diaphragm is in its empty position 38$a$, then, because the diaphragm has a finite spring constant, the pressure in the reservoir is less than when the diaphragm is extended fully to position 38$b$. The effect of this changing pressure is shown in FIG. 2. Specifically, the prior art pulsatile pump has a smaller stroke volume for lower pressures in the fluid reservoir (with diaphragm near position 38$a$) and a higher stroke volume corresponding to a greater pressure in the reservoir corresponding to the diaphragm at postion 38b. The diaphragm of the pump has a finite compliance and when at position 12b has a greater upward deflection due to reservoir pressures therefore allowing a greater amount of fluid into the pump chamber 18, and providing a greater stroke volume. Likewise, lower stroke volumes correspond to lower reservoir pressures (as seen in FIG. 2) because there is less upward deflection at 12b of the compliant diaphragm when there is lower reservoir pressure.

Another reason the prior art pumps have higher stroke volume at higher reservoir pressures is a result of the inlet and outlet valves having fairly high flow resistances. Particularly, this is because they are open for extremely short times ($\simeq 1$ ms) which is associated with high flow rates and comparatively high flow resistance. Therefore, when the pressure in the reservoir is higher, for the same pressure in the exit tube 24, we will get a higher differential pressure across the valves causing a greater flow rate across the comparatively high flow resistance of the valves and therefore a higher pump stroke volume. Similarly, at lower reservoir pressures, the stroke volume will be less. Thus the curve of FIG. 2 shows typical stroke volume variations for this type of prior art pump.

Figure 3:
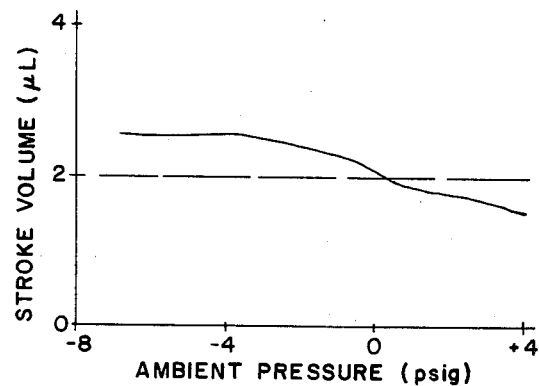
FIG. 3 is a graph showing the effect of ambient pressure on stroke volume for such prior art pumps.

FIG. 3 contains a curve which illustrates the effect of ambient pressure on stroke volume for such prior art pumps. When ambient pressure is increased, the pressure in the exit tube 24 is increased and the diaphragm at 12a is deflected upward, thereby decreasing the stroke volume. Most pumps are designed with a hard stop for the cylinder at its full upward position 10b so that there is less deflection of the compliant diaphragm at its 12a position as compared to its 12b position where there is no constraint on the cylinder at its full downward position 10a. Thus the effect of increasing ambient pressure on the exit tube is to decrease stroke volume as seen in FIG. 3.

Also, the flow rate through the inlet and outlet valves, which depends on differential pressure, will vary with changes in ambient pressure. Thus higher ambient pressure (at a constant reservoir pressure) will result in a differential pressure across the outlet valve 22 and, therefore, lower flow rates through the valve 22 and, therefore, lower stroke volume as seen in FIG. 3. Conversely, lower ambient pressures lead to higher differential pressure across the outlet valve 22 and, therefore, a higher stroke volume.

For the typical prior art, two valve, diaphragm pump illustrated in FIG. 1, any bubble that enters the reservoir can enter the pump. If a large enough bubble enters the pump, it will stop the pumping of the incompressible liquid because the gas can compress fully before sufficient pressure is generated to open the inlet and/or the outlet valve(s). This condition is highly undesirable if the pump is implanted in humans.

Since the valves in prior art Fig. 1 have a significant length, the overall height of the pump is comparatively great, resulting in an undesirable increase in thickness of the implanted pump.

Figure 4:
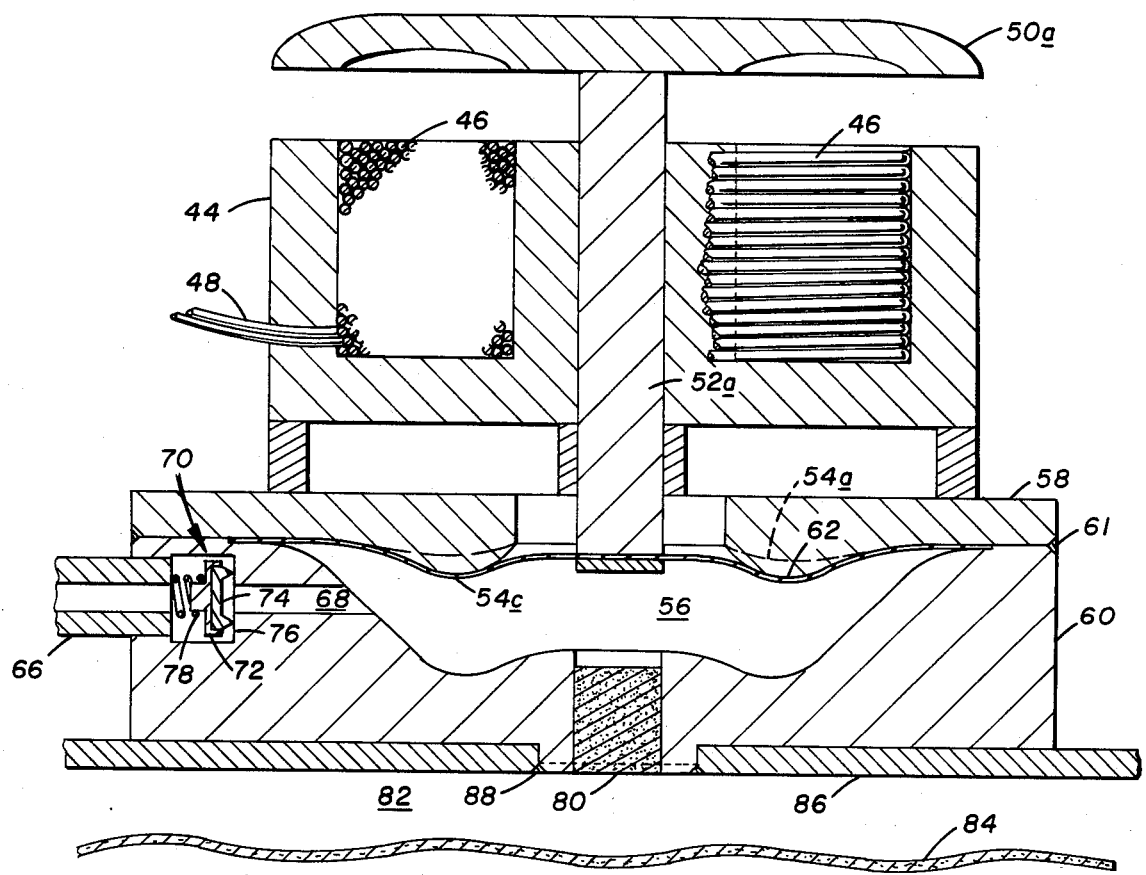
FIGS. 4 and 5 show the present invention of a single valve pump with improved capabilities as to accuracy of delivery flow rate and freedom from compromised operation because of air bubbles.
Figure 5:
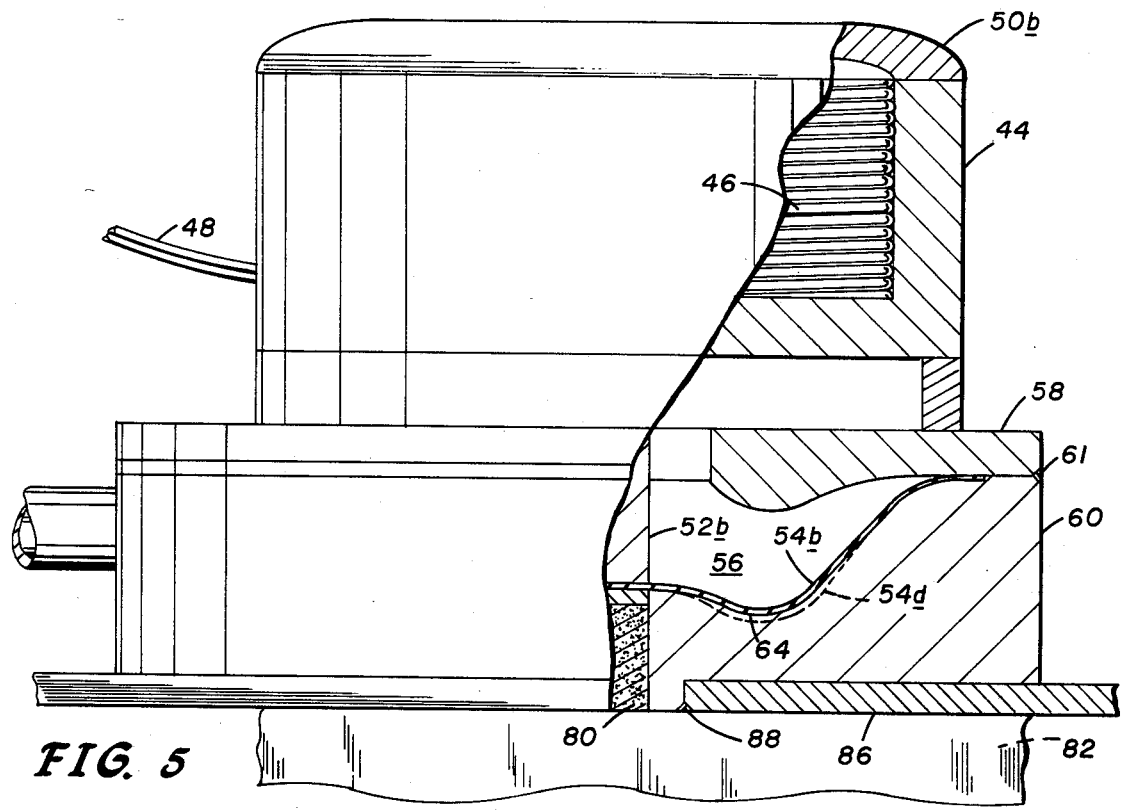

FIGS. 4 and 5 show a specific embodiment of a single valve diaphragm pump as taught by the present invention with FIG. 4 representing the rest position and FIG. 5 representing the actuation position. This pump offers several operating advantges when compared to the prior art two valve-pump shown in FIG. 1. In FIG. 4, a magnetic solenoid consisting of a magnetic core 44 has contained within its cylindrical structure a solenoid coil 46 with lead out wires 48. When a pulse of electrical current goes through the coil 46 via the lead out wires 48, then the magnetic core 44 is magnetized and the magnetic armatures goes from its normal rest position 50a (see FIG. 4) to its actuated position 50b (see FIG. 5). In doing so, a central cylinder attached at the center of the armatures moves downward from its rest position 52a (FIG. 4) to its fully actuated position 52b. (see FIG. 5). This in turn results in the motion of the diaphragm from its normal or rest position 54a (see FIG. 4) to its full stroke (actuated) position 54b (see FIG. 5). After the solenoid coil is actuated with a pulse of electricity, the natural spring force of the diaphragm (or a separate spring not shown) returns the diaphragm to its normal or rest position 54a (see FIG. 4) thus causing the pump chamber volume 56 to be first decreased on the downward (actuated) stroke and then increased on the upward stroke.

Unlike the prior art solenoid pump design shown in FIG. 1, the pump housing consists of two parts; an upper portion 58 and a lower portion 60 welded together by a weld 61. Also unlike the conventional pump, the upper portion 58 (see FIG. 4) has an inner surface 62 that contacts the diaphragm at its rest position 54a, and the lower portion 60 (see FIG. 5) has an inner surface 64 that contacts the diaphragm at its fully extended (full downward) position 54b. Furthermore, if the surface 62 of the upper portion 58 were not present, the diaphragm would normally, by its own spring force, move up until the diaphragm reached position 54c as shown by the dotted line in FIG. 4. Likewise, if not for the surface 64 of the lower portion 60, the diaphragm would be extended further to the dotted line 54d shown in FIG. 5. In this way, the diaphragm, even though it does itself have compliance, will not be deformed, for reasonable variations in reservoir pressure or ambient pressure variations seen at the exit tube 66 because it is backed up by the rigid surfaces 62 and 64. Therefore, the stroke will have much smaller variations in stroke volume as a function of reservoir pressure than for prior art pumps which depend on the amount of fluid in the reservoir, as seen in FIG. 2. Likewise, variations in stroke volume due to changes in ambient pressure will also be markedly decreased by employing the invented pump design.

To describe the manner by which liquid is pumped using the invented design of FIGS. 4 and 5, let us begin with the diaphragm at its upward (rest) position 54a (see FIG. 5). At this point, the pump chamber 56 is at its maximum volume. Upon actuation of the solenoid coil 46, the diaphragm is very rapidly (in approximately one millisecond) moved to position 54b thus decreasing the pump chamber volume to its smallest value and forcing liquid through the exit port chamber 68, the exit valve 70 and then the exit tube 66. The exit valve consists of a poppet having a metallic portion 72, an elastomer portion 74 that is forced against a valve seat surface 76 by a valve spring 78. A ceramic filter 80 having a very high resistance to flow will allow a small amount of fluid (less than 10 percent of the stroke volume) to go through it into the reservoir 82 on the downward stroke. A well designed filter 80 with a very high flow resistance will only allow one percent or less liquid volume through it during the downward stroke of the diaphragm. Fluid flowing into the reservoir 82 on the downstroke tends to dislodge from filter 80 any particulate in the reservoir which might otherwise clog filter 80.

After the diaphragm has reached its fully extended position 54b (see FIG. 5), the natural spring force of the diaphragm will begin moving it upward toward position 54a. On the up (intake) stroke, liquid is drawn from reservoir 82 through filter 80 into the pump chamber 56. As liquid is drawn from the reservoir, the flexible diaphragm 54 moves upward therefore reducing the volume of liquid in reservoir 82. The resistance of the filter 80 is sufficiently high so that the pump upstroke requires from 0.1 second to several seconds depending on the pore size, length and area of the filter; i.e. depending on the filter's flow resistance. The reservoir upper plate 86 is joined to the lower pump portion 60 by the weld 88.

For the prior art two-valve pump the finite resistance to flow of the inlet valve 16 of FIG. 1 is important because all flow must be accomplished in approximately 1 ms, thus a higher reservoir pressure leads to a higher flow rate through the inlet valve and hence higher stroke volume. For the invented design of FIGS. 4 and 5, at least 15 seconds can be allowed for the diaphragm to reach its normal (rest) position 54a, therefore, the resistance of the ceramic filter 80 will not be of consequence. Thus, we have another reason (besides the effective elimination of diaphragm compliance) as to why the design of FIGS. 4 and 5 should lead to much lower variation of stroke volume as a function of reservoir pressure.

In operation, the diaphragm will move precisely and repeatably from 54a to 54b irrespective of expected changes in ambient pressure. Therefore, the invented pump as illustrated in FIGS. 4 and 5, really approaches a positive displacement pump whose displacement is independent of ambient pressure. Therefore, the invented pump has less variations in stroke volume with ambient pressure as compared with the results for the prior art design.

Another advantage of the present invention is that the ceramic filter 80 can have a sufficiently small pore size, e.g., 1-20 microns, that bubbles that get into the reservoir will be prevented from entering the pump chamber 56. Since any significant bubble in the pump chamber 56 will prevent the output valve 70 from opening, it is very important to prevent bubbles from getting into the pump chamber 56.

Another advantage of the present invention is that the single valve (outlet valve 70) can be placed on the side of the pump body 60, thereby reducing the height of the pump, therefore allowing a thinner overall height for an implantable infusion pump. Furthermore, the exit valve spring 78 can be made longer when the valve is on the side of the pump body 60, thereby making the adjustment of the exit valve 70 seating force less critical and, therefore, less difficult to manufacture.

Various other modifications, adaptions and alternative designs are, of course, possible in light of the above teachings. Therefore, it should be understood at this time that within the scope of the appended claims, the invention may be practiced otherwise than specifically described herein.

What is claimed is:
1. A positive displacement pump, comprising:
a pump chamber;
a passageway providing bidirectional fluid communication between said pump chamber and a source of liquid to be pumped;
an outlet valve and conduit in fluid communication with said pump chamber;
a variable volume means for increasing the volume of said pump chamber during an intake stroke and for decreasing the volume of said pump chamber during an output stroke, wherein liquid is drawn through said passageway into said pump chamber during said intake stroke, said output stroke being rapid compared to said intake stroke; and,
an inlet filter means having a flow resistance characteristic which is identical for both inflow and outflow and is positioned in said passageway for permitting filling of said pump chamber at a first, comparatively slow rate during said intake stroke and cooperates with said variable volume means for generating sufficient fluid pressure in said pump chamber during a second, comparatively rapid output stroke to open said outlet valve and eject a substantial volume of liquid from said pump chamber.

2. The apparatus of claim 1, wherein said variable volume means comprises:
a diaphragm defining a boundary of said pump chamber;
a means for moving said diaphragm during said output stroke from a rest position wherein said pump chamber has a maximum volume to an actuation position wherein said pump chamber has a minimum volume; and,
a means for returning said diaphragm during said intake stroke to said rest position.

3. The apparatus of claim 2, further comprising a housing having a first wall and a second wall, said diaphragm contacting along the surface of said first wall when in said rest positioning thereby conforming to the contour of said first wall, said diaphragm contacting along the surface of said second wall when in said actuation position thereby conforming to the contour of said second wall.

4. The apparatus of claim 1, further comprising a housing having an upper wall and a lower wall, and said variable volume means further comprising:
a diaphragm operably attached to said housing and positioned between said upper wall and said lower wall, said diaphragm and said lower wall defining a boundary of said pump chamber, said diaphragm reciprocally movable from a first rest position where said diaphragm contacts along the inner surface of said upper wall thereby conforming to the shape of said inner surface of said upper wall to an actuation position where said diaphragm contacts along the inner surface of said lower wall thereby conforming to the shape of said inner surface of said lower wall;
a means for moving said diaphragm during said output stroke from said rest position where said pump chamber has a certain maximum volume value to said actuation position where said pump chamber has a certain mininum volume value; and,
a means for returning said diaphragm to said rest position during said intake stroke.

5. The apparatus of claim 3 or 4, wherein said means for moving further comprises:
a solenoid coil for providing a magnetic field in response to a current pulse; and,
an armature means mechanically coupled to said diaphragm, for moving said diaphragm from said rest position to said actuation position in response to said magnetic field.

6. The apparatus of claim 5, wherein said means for returning said diaphragm to said rest position comprises the natural spring force of said diaphragm.

7. The apparatus of claim 1, wherein said inlet filter means is a filter having sufficiently small pore size to prevent bubbles of gas from entering said pump chamber.

8. The apparatus of claim 7, wherein said input fiter means is a ceramic filter.

9. The apparatus of claim 8, wherein said ceramic filter has a pore size of 1 to 20 microns.

10. The apparatus of claim 6, wherein said outlet valve and conduit further comprises:
   an exit port chamber in fluid communication with said pump chamber;
   a spring loaded check valve in fluid communication with said exit port chamber; and,
   an exit tube in fluid communication with said spring loaded check valve, wherein said spring loaded check valve is biased to allow fluid flow from said pump chamber into said exit tube in response to fluid pressure build-up in said pump chamber during said output stroke.

11. A positive displacement pump, comprising:
   a pump housing having an upper wall and a lower wall;
   a diaphragm operably attached to said housing and positioned between said upper wall and said lower wall, said diaphragm and said lower wall defining the boundary of said pump chamber, said diaphragm reciprocally movable from a rest position where said diaphragm contacts along the inner surface of said upper wall thereby conforming to the shape of said inner surface of said upper wall to an actuation position where said diaphragm contacts along the inner surface of said lower wall thereby conforming to the shape of said inner surface of said lower wall;
   an electromagnetic means for moving said diaphragm during an output stroke from said rest position wherein said pump chamber has a certain maximum volume to said actuation position wherein said pump chamber has a certain minimum volume;
   a spring means for returning said diaphragm during an intake stroke to said rest position, said output stroke being rapid compared to said intake stroke;
   a passageway providing bidirectional fluid communication between said pump chamber and a source of liquid to be pumped;
   an outlet valve and conduit in fluid communication with said pump chamber; and,
   an inlet filter means having a flow resistance characteristic which is identical for both inflow and outflow and is positioned in said passageway for permitting filling of said pump chamber at a first, comparatively slow rate during said intake stroke and cooperates with said variable volume means for generating sufficient fluid pressure in said pump chamber during a second, comparatively rapid output stroke to open said outlet valve and eject a substantial volume of liquid from said pump chamber.

* * * * *